United States Patent
Balbi et al.

(10) Patent No.: US 9,629,612 B2
(45) Date of Patent: Apr. 25, 2017

(54) BIOMEDICAL IMAGE RECONSTRUCTION METHOD AND APPARATUS

(71) Applicant: Esaote SPA, Milan (IT)

(72) Inventors: Luca Balbi, Genoa (IT); Amedeo Buonanno, Sant'Arpino (IT); Paolo Pellegretti, Genoa (IT); Andrea Serra, Genoa (IT); Rosario Varriale, Napoli (IT); Marco Vicari, Freiburg Im Breisgau (DE)

(73) Assignee: ESAOTE SPA, Genoa (IT)

( * ) Notice: Subject to any disclaimer, the term of this patent is extended or adjusted under 35 U.S.C. 154(b) by 276 days.

(21) Appl. No.: 13/886,016

(22) Filed: May 2, 2013

(65) Prior Publication Data

US 2013/0310678 A1    Nov. 21, 2013

(30) Foreign Application Priority Data

May 4, 2012   (IT) .......................... GE2012A000048

(51) Int. Cl.
| | |
|---|---|
| *A61B 5/055* | (2006.01) |
| *A61B 8/08* | (2006.01) |
| *G01R 33/561* | (2006.01) |
| *G01R 33/56* | (2006.01) |
| *G01R 33/565* | (2006.01) |

(52) U.S. Cl.
CPC ................ *A61B 8/52* (2013.01); *A61B 5/055* (2013.01); *G01R 33/561* (2013.01); *A61B 8/5207* (2013.01); *G01R 33/5608* (2013.01); *G01R 33/56509* (2013.01); *G01R 33/56563* (2013.01)

(58) Field of Classification Search
CPC ......... A61B 5/055; A61B 8/52; A61B 8/5207; G01R 33/5608; G01R 33/561; G01R 33/56509; G01R 33/56563
See application file for complete search history.

(56) References Cited

U.S. PATENT DOCUMENTS

| | | | | |
|---|---|---|---|---|
| 2008/0197842 | A1* | 8/2008 | Lustig ................. | G01R 33/561 324/307 |
| 2009/0262996 | A1* | 10/2009 | Samsonov ......... | G01R 33/4818 382/130 |
| 2011/0006768 | A1* | 1/2011 | Ying ................... | G01R 33/5611 324/309 |

(Continued)

*Primary Examiner* — Ruth S Smith
(74) *Attorney, Agent, or Firm* — Buchanan Ingersoll & Rooney PC

(57) ABSTRACT

A method of reconstructing an MRI or ultrasound biomedical image, based on compressed sensing includes exciting a body under examination; acquiring image data from the generated signals, wherein the signals are acquired by pseudo-random undersampling; reconstructing the image using a nonlinear iterative algorithm for minimizing an optimization function containing one or more terms for image data sparsity in one or more predetermined domains with a data fidelity constraint term ensuring fidelity to the acquired image data; wherein two or more sets of image data are acquired from the generated signals, each data set being acquired in a different undersampling scheme and/or a different acquisition mode such as to make expected and unavoidable artifacts incoherent; each of the acquired image data set is multiplied by a correction matrix $\Delta$.

35 Claims, 8 Drawing Sheets

(56) References Cited

U.S. PATENT DOCUMENTS

| | | | | |
|---|---|---|---|---|
| 2011/0142316 A1* | 6/2011 | Wang | .................... | G06T 11/006 |
| | | | | 382/131 |
| 2011/0282181 A1* | 11/2011 | Wang | ................... | A61B 5/0095 |
| | | | | 600/407 |
| 2012/0281896 A1* | 11/2012 | Aspelmeier | ........... | G06T 11/006 |
| | | | | 382/131 |

* cited by examiner

9

BIOMEDICAL IMAGE RECONSTRUCTION METHOD AND APPARATUS

CROSS-REFERENCE TO RELATED APPLICATIONS

The present application claims the priority of Italian Patent Application No. GE2012A000048, filed on May 4, 2012, the entire contents of which is incorporated herein by reference.

TECHNICAL FIELD

The present disclosure relates to a method of reconstructing an MRI or ultrasound biomedical images. More specifically, reconstructing an MRI or ultrasound biomedical images, based on compressed sensing and comprising the steps of:

a) exciting a body under examination with radio-frequency (RF) or ultrasound (US) pulses for generating signals;

b) acquiring image data from said generated signals, wherein said signals are acquired by pseudo-random undersampling;

c) reconstructing said one or more images using a nonlinear iterative algorithm for minimizing an optimization function containing one or more terms for image data sparsity in one or more predetermined domains with a data fidelity constraint term ensuring fidelity to the acquired image data.

BACKGROUND

Methods are known and used for reconstructing images from data sets obtained by undersampling, and use a technique known as Compressed Sensing (CS), having the purpose of reducing the amount of data to be sampled during acquisition.

The basic principle of CS consists in measuring a few critical coefficients of a compressible signal and then reconstructing it by an iterative optimization process.

This reconstruction procedure is based on the solution of the following constrained optimization problem;

$$\min \|\Psi m\|_1 s.t. \|F_u m - y\|_2 \leq \epsilon, \quad (1)$$

where m is the reconstructed image, $\Psi$ is the transform in a domain, where the result of the transform is sparse, preferably the Wavelet transform, $F_u$ is the Fourier transform with the same undersampling as the acquired k-space y. This procedure tends to an image m whose Wavelet transform is sparse and whose k-space is coherent with the acquired k-space (fidelity term).

The term of fidelity to the acquired image data is a rank-2 minimization, i.e. sum of the squares of the moduli, the difference between the image data obtained at each iteration step and the actually acquired image data.

A further term relating to a further space in which the image is mapped in sparse mode is the term of the finite differences of the image, usually known as Total Variation (TV), whose introduction causes the equation (1) to become:

$$\min \|\Psi m\|_1 + \alpha TV(m) s.t. \|F_u m - y\|_2 \leq \epsilon, \quad (2)$$

Using Lagrange multipliers, the constraints may be introduced in the function to be minimized, which becomes:

$$f = \|F_u m - y\|_2 + \lambda_1 \|\Psi m\|_1 + \lambda_2 TV(m), \quad (3)$$

where the first term is the term of fidelity to the acquired image data, the second term is the term of image data sparsity in a predetermined domain, preferably in the Wavelet domain, and the third term is the term of finite differences of the image, or Total Variation.

Methods are known which use CS in MRI and ultrasound imaging.

Nevertheless, prior art methods are directed to undersampled acquisition and reconstruction either of individual images from individual sets of image data, or dynamic time-based images.

However, in many situations, multiple sets of image data are acquired, for a number of reasons.

In these situations, prior art methods can only reduce acquisition time by undersampling, but no use is made of redundant information for artifact correction, and there is no change of the algorithm for incorporating therein a prior knowledge of such artifacts to be removed.

SUMMARY

The method of the present disclosure has the object of overcoming the limitations of prior art methods, by method as described hereinbefore, wherein two or more sets of image data are acquired from said generated signals, the index of each image data set being i in the equation below, each data set being acquired in a different undersampling scheme, denoted by $u_i$ in the equation below, and/or a different acquisition mode such as to make expected and unavoidable artifacts incoherent;

each of the acquired image data set is multiplied by a correction matrix $\Delta_i$, which is calculated from a mathematical model of expected artifacts according to prior knowledge of such artifacts, for adjusting said fidelity term in such a way that the fidelity term ensures fidelity of the reconstructed image to the corrected acquired image data as in the following equation:

$$f = \sum_i \|F_{u_i} m - \Delta_i y_i\|_2 + \lambda_1 \|\Psi m\|_1 + \lambda_2 TV(m);$$

for each iteration of said nonlinear iterative algorithm the data sets are processed to generate a combination image m which will therefore be faithful to the acquired data but not to the incoherent artifacts, thereby leading to suppression of said artifacts.

Even though just one image can be reconstructed, this reconstruction is based on the acquisition of two or more different data sets referring to the same image.

The non-linear iterative reconstruction algorithm combines the information carried by the different data sets referring to the same image and provides the final image.

Thus artifacts which are unavoidable are formed incoherent, so that they can be more effectively identified, and more easily suppressed.

The artifacts to be suppressed are potentially present in all the acquired data sets for every image, but these artifacts are mutually incoherent and it is not necessary to specifically identify and/or characterise them in the image.

The image reconstruction algorithm implies a destructive interference of the incoherent artifacts, whatever and wherever they are.

Hence the resulting final image is devoid or less affected by artifacts that would spoil the quality of the images obtained by singularly reconstructing each data set.

The mentioned artifacts are unavoidable and incoherent, because due to temporary, environmental and/or physiological sources. Moreover, these artifacts are mostly not reproducible and not acquisition-synchronised. In a first variant embodiment, the sets of image data are k-spaces generated by 2D or 3D MRI acquisitions.

Examples of artifacts are:

the external field interference due to movement of metallic bodies, power spikes of the electric system, broadcast etc.

imaged living being blood and cerebrospinal fluid pulsation, breathing, swallowing, movements in general etc.

Further source of incoherent artifacts are the different response of the scanner in terms of eddy current compensation, thermal stress, mechanical stress, etc., to the specific undersampling trajectory in k-space used for the different data sets referring to the same image to be reconstructed.

With the term undersampling schemes it is intended for example the different trajectories in k-spaces that skip different locations in k-space.

With the term acquisition mode it is intended for example Partial Fourier Acquisitions, Fast Spin Echo multiple-series acquisitions, multiple-average acquisitions, multiple-receiving-channel acquisitions etc.

Some artifacts are due to problems which are external to the scanner, like for example external field interference or power spikes, or like movements of the patient.

In this case there is no acquisition mode that should be set up, but it is sufficient to acquire the data sets in different times to probably obtain incoherent artifacts.

Some other artifacts are due to problems inherent to the scanner and the acquisition sequences, like for example eddy currents, T2 decay of the tissues, stationary states, so that different acquisition modes can lead to incoherent artifacts.

Each image is obtained by the specific reconstruction algorithm jointly processing two or more data sets and each data set is acquired according to a peculiar acquisition and/or undersampling mode.

This mode combination can be different for every data set. Thus, the signal acquired to build up every data set has different features that can be exploited to properly suppress incoherent artifacts.

Basically every data set can be characterized by a peculiar undersampling scheme, aimed to make the suppression of the incoherent artifacts as efficient as possible and the resulting speed-up of the whole data acquisition as large as possible.

The characteristics as described below are adapted for application both to high field acquisitions and, in a more particularly advantageous manner, in low field acquisitions.

As mentioned above, in various cases multiple k-spaces may be acquired.

In a first exemplary embodiment, sequential averaging is performed between k-space data sets.

The data sets refer to the same image and are acquired according with different acquisition and/or undersampling modes, properly chosen according to the purpose of image quality enhancement and acquisition speed-up.

Each successive signal average is only acquired after acquisition of the previous k-space data set.

In the case of sequential averages any type of sequence can be used and the artifacts due to physiological causes, as for example motion, are mutually incoherent.

In a second exemplary embodiment phase-cycling for b-SSFP (balanced steady-state free precession) sequences is performed.

The redundant information obtained from the various phase-cyclings may be utilized to enhance sparsity.

This is because the use of CS for reconstructing phase cycling differences affords higher acceleration factors, as the difference images contain less information and are more compressible.

Furthermore, the time that has been saved by undersampling may be at least partially used to increase the number of phase cycles.

This may in turn allow the use of more refined methods to fuse the individual images that show the typical banding artifacts of bSSFP (balanced steady-state free precession) sequences.

In a third exemplary embodiment, Fast Spin Echo (FSE) excitation sequences are used.

The acquisition of k-spaces using T2-weighted FSE sequences occurs in a segmented manner, with each sample being sampled by an echo of the echo train of the sequence.

Due to T2 decay, the echo amplitude decays along the echo train, and the mapping of echoes of two or more k-space data sets may be permuted in their arrangement, to obtain different envelope profiles in the phase direction.

Particularly, k-space echo segmentation may be selected to impart a sine modulation of the k-space in the phase direction.

In this particular modulation, the center of the k-space is acquired by an echo preceded by echoes encoded with relatively low encoding values.

This has been found to be particularly advantageous in low-field acquisitions, such as in dedicated systems, for reducing possible artifacts caused by residual eddy-current effects.

Indeed, under the same acquisition conditions, the CS technique involves undersampling especially at the edges of the k-space, thereby further enhancing this advantageous condition.

In FSE sequences with multiple series, i.e. k-space acquisitions with different encoding strategies, multiple k-spaces are acquired for the same image.

This allows reconstruction of images with different artifacts, as both the Point Spread Function (PSF) and the undersampling schemes or modes may be conveniently changed.

In one embodiment, the echoes of two or more k-spaces are permuted in their arrangement to obtain two k-spaces with the same sine profile.

In a further embodiment, the echoes of two or more k-spaces are permuted in their arrangement to obtain two or more k-spaces symmetric with respect to the center, at least one of such k-spaces only containing the concave portions, and at least another of such k-spaces only containing the convex portions.

In a further embodiment, a single complete non-undersampled k-space is acquired, for use as a reference in the iterative algorithm.

This is ensured by the fact that this k-space is free of any undersampling artifact.

In yet another embodiment, a complete k-space is used, which is obtained by multiple averaging with different undersampling schemes.

The data obtained from such modes contains the same noise and incoherent artifacts, as different undersampling schemes or modes are used, and different violations of the CPMG condition may occur and the artifacts which are introduced by the same violation of the CPMG condition are different because they are in different zones of the k-space.

In this situation the so-called FSE Star technique is only a peculiar case of acquisition with multiple series.

The FSE Star technique is disclosed in Patent Application GE2012A000022 by the Applicant hereof and concerns filling of multiple k-spaces to generate a single k-space, partial averaging with multiplicative factors for different portions of the k-space data sets being performed, in which lower-intensity signals corresponding to the same phase-encoding gradient are summed together and averaged, whereas higher-intensity signals are left unaveraged.

Said multiplicative factors can be introduced into the optimization carried out by the method of the present disclosure, for example incorporating them into the correction matrix $\Delta$.

According to an embodiment of the present disclosure, for each step of the nonlinear iterative algorithm the following steps are carried out:

d) all sets of image data are independently processed with a standard CS iteration, and a set of images is obtained e) combining the obtained images by an image fusion technique;

f) using the differences between the image obtained by image fusion and the original images to identify the required corrections based on the expected artifacts;

g) incorporating the identified corrections into the correction matrix $\Delta$ to be used in the next iteration.

The optimization procedure may be carried out for each of the N k-spaces being reprocessed, according to the following function $$f = \sum_{i=1}^{N} \|F_u m_i - y\|_2 + \lambda_1 \|\Psi m_i\|_1 + \lambda_2 TV(m_i) \quad (4)$$

At each iteration the image $m_i$ may be appropriately fused into a final image m to promote the correlated characteristics, assuming that these are the actual characteristics of the object being imaged.

Likewise, the non-correlated details, which are mainly artifacts, are suppressed.

All the acquisitions describe the same object, but suffer from different artifacts.

Two embodiments of this additional implementation may be provided.

In a first embodiment, sparsity and TV terms may be also added for $m=\Sigma m_i$ (where $\Sigma$ represents an image fusion technique).

$$f = \sum_{i=1}^{N} \|F_u m_i - y\|_2 + \lambda_1 \|\Psi m_i\|_1 + \lambda_2 TV(m_i) + \lambda_3 \|\Psi m\|_1 + \lambda_4 TV(m) \quad (5)$$

In a second embodiment, the term $\|m_i - m\|_2$ is added to the function, where the derivative may be approximated using the m value obtained from the previous iteration.

This means that the new m is cleared of artifacts by an image fusion technique, and that $m_i$ shall tend to m.

The non linear fusion of the acquired images or of the related k-space data sets allows to better guide the constrained reconstruction.

In a further embodiment, in reduced field-of-view MRI, data normalization is performed by exclusion or smoothing of values exceeding a predetermined threshold.

This normalization is particularly advantageous in that hyperintensities caused by magnetic field inhomogeneities are excluded in Spin-Echo sequences.

Strong magnetic field inhomogeneities may drastically deteriorate image quality as they cause mismatch of the sparsity term of the function.

A magnet structure with an imaging volume is generally provided, the magnet structure having one or more apertures for access to said imaging volume, the center of the magnet structure being identified as the central position of the imaging volume among these apertures.

In a further embodiment, data normalization is performed by weighting the image with an attenuation factor that increases with the distance from the center of the magnet structure.

In a fourth exemplary embodiment, k-spaces of images with different contrast information are acquired, said image fusion technique comprises the use of a map of the physical quantity that drives the difference among the images.

The physical quantity that drives the difference among the images can be for example T2 for a multi-echo spin-echo, or the logarithm of the ratio between the two images for a Double Echo Steady State Gradient Echo.

A number of MRI applications exist, in which multiple k-spaces are acquired, each containing different contrast information. This occurs, for example, in either Spin Echo or Gradient Echo Multi Echo imaging techniques, possibly of the steady-state type.

In the standard framework, the output may be the individual image, consisting in a weighted average of the acquired images.

According to the present disclosure, with images having different contrasts, optimization involves all the images, i.e. the acquired images and their combinations.

The image obtained by image fusion may assist convergence in the optimization process, with artifact suppression.

The main purpose is to find an image fusion technique that is able to fuse information that may be misleading, due to the changing contrast in the images.

In order to acquire images with different contrast information, TE, TR or flip angle, as an example, can be varied.

In a preferred embodiment, the selected image fusion technique consists in mapping physical quantities that do not change with the images.

Thus the images are different, but since a joint optimization is required, the iterative algorithm can use the physical quantity that drives the difference among the images as the image fusion technique that guides the iterative process.

Such physical quantity could be for example T2, but also T1 if a different TR is chosen, or different steady states if different flip angles are chosen.

In a first embodiment, multi-echo spin-echo sequences are used, and the image fusion technique comprises T2 mapping by monoexponential best-fit of the signal for each pixel or voxel, corresponding T2 error mapping, the iterative reconstruction process including rank-2 minimization of the T2 error map.

In the same iteration, the resulting map should be "smooth" and "sparse" in the Wavelet domain.

In this example, the calculation of T2 is exact, except for some negligible intrinsic errors.

In a further embodiment, a Double Echo Steady State Gradient Echo sequence is used, and the image fusion technique comprises the calculation of a map of the logarithm of the ratio between the two images. This approximately corresponds to T2.

This map should also be "smooth" and "sparse" in the Wavelet domain.

In this case, the calculation of T2 is not exact, and some approximation is needed.

In a further embodiment, the generated map, which is used as an instrument for joint optimization of different images, is used as an output map.

Alternatively, the final map may be obtained by complete process modeling, whereas the approximate map is only used for optimization and artifact suppression.

The acquired data are further processed for improved results, by maximized utilization of prior knowledge of artifact features, like in the case of artifacts caused by flow, motion and violations of the CPMG condition.

The basic idea is that the fidelity term must use the "reality" as reference, i.e. the ground truth.

If the ground truth is not exactly represented by the data that are actually acquired according to some undersampling scheme, then the method can be further refined by correcting the acquired data on the basis of the artifact prior knowledge.

Prior knowledge on expected artifacts is obtained, for example:
- by comparing the images coming from a trivial reconstruction of the different data sets and identifying the structure that are present just in some of the images: these are very likely to be artifacts. Once identified the artifact, its features in term of position, intensity, phase, repetition are straightforward.
- by comparing the images coming from the trivial reconstruction of the different channels of each data set with the corresponding channel sensitivity map: if some non-noise structure is present in an area where the channel is not able to pick up signal (i.e. where the sensitivity map is null), than that structure is likely to be an artifact.
- by system/sequence calibrations, that provide information about the MRI signal.
- by analysing the cross-correlation of portion of the k-space according to its segmentation during acquisition.

Once some of the features of the artifacts are known, then the related structures can be "filtered away", both in k-space and in the image domain. A proper exploitation of all possible a priori knowledge concerning artifact features is obtained by multiplying the sets of image data a correction matrix $\Delta$ for adjusting the fidelity term according to prior knowledge of the expected artifacts.

Such adjustment may be a change or improvement of the fidelity term.

Exceptions to the constraint of data fidelity with the acquired data are allowed, according to prior knowledge of the expected artifacts.

To provide an easy example, suppose to know the artifact structure in the image domain, then, the reference image in the fidelity term can be multiplied by a mask reducing the severity or even getting rid of that artifact's structure. Likewise, phase abnormalities and/or fluctuation in k-space can be suppressed. In a first exemplary embodiment, the correction matrix $\Delta$ is used for correcting motion artifacts and is calculated by estimating a predetermined displacement value in the read and phase direction in the real world and incorporating it as a phase shift in the k-space data sets at a predetermined acquisition time.

This leads to a well-defined correction matrix $\Delta$ which falls within limit values.

The search for an optimal correction matrix $\Delta$ may also be incorporated in the matrix or determined beforehand from the estimated current of the image m deriving from the image fusion process.

Therefore, for motion artifact correction, two k-space data sets may be deemed to be equivalent if they only differ in terms of displacement of the image in the read (x) or phase (y) direction.

Application of the shift theorem proves to lead to a "phase ramp" in the k-space; an incoherent pattern of "phase ramps" causes known artifacts.

Therefore, an additional correction operator $\Delta_{mac}$ may be applied $$\Delta_{mac}(k;n^s,n^e,\delta x,\delta y)=ke^{i(k_x\delta x+k_y\delta y)}|_{n^s\leq nph\leq n^e},$$

where the k-space k is sampled on the coordinates $k_x$ and $k_y$ and has undergone an amplitude displacement $(\delta x,\delta y)$ that occurred during acquisition of contiguous phase encoding blocks, starting at the $n^s$-th phase encoding and ending al $n^e$-th phase encoding.

A total operator, which describes the whole displacement during acquisition, may be constructed as a product of partial operators:

$$\Delta_{mac}(k) = \prod_i \Delta_{mac}(k; n_i^s, n_i^e, \delta x_i, \delta y_i)$$

The search for an optimal operator may be based on minimization of known image metrics that describe the entity of displacement artifacts.

It should be noted that TV minimization, which is inherent in the CS technique, has a similar effect. Therefore, a possible implementation may exclude the calculation of particular metrics, and hence avoid an additional computational burden.

In a second example, the correction matrix $\Delta$ is used for correcting k-space inconsistencies induced by echo position and phase errors in the read and phase direction in a Fast Spin Echo (FSE) acquisition.

Thus, the CPMG conditions may be improved by forcing $\Delta$ to match the signal of an additional TR, i.e. a TR acquired without phase encoding.

In FSE sequences, the characteristic segmentation of the k-space provides accurate information on the correlation of possible echo position errors along the read and phase direction in the k-space.

This correlation may be used to control a heuristic search aimed at recovering any misalignment of the various segments, that are sampled by different echoes.

This involves a change of the fidelity term, considering an actual k-space after the Fourier transform in the read direction $\|F_u m_i - y_i \Delta\|_2$, wherein the j-the column in $\Delta$ (phasor matrix) is in the form $$e^{i\left(\Phi+\delta\left(j-\frac{nfas}{2}\right)\right)}.$$

Furthermore, the parity of echoes in the echo train may be also used for improved identification of the local correction sign.

In a further embodiment, the correction matrix $\Delta$ is used for correcting T2 decay induced artifacts in Fast Spin Echo (FSE) sequences.

Thus the different decays T2 incurred by the k-space segments, i.e. echoes at different times, may be accounted for.

The magnitude of $\Delta$ may be changed according to the form $e^{(-j/\alpha)}$, where j is the echo/segment index and $\alpha$ has the size of the samples being read, and its correction values may be limited to a predetermined range, to avoid any possible overcompensation, and derived from the information contained in the additional TR.

The term $\alpha$ is the key variable to be optimized in the FSE Star technique, in which it only depends on the number of echoes and not on the echo position in the read direction, for better equalization of the noise level.

Furthermore, $\alpha$ may be appropriately filtered in the read direction, preferably by a dedicated TV term.

In one embodiment, the domain $P(x,k_y)$ is obtained by the Fourier transform of the k-space in the read direction.

Based on the analyses of the additional TR, the following operations are executed on $P(x,k_y)$:

Filtering along x
Robust fitting of $\alpha(x)$. SNR is increased and undesired blurring is prevented, as it acts in the phase direction and not along the read gradient.
Wide smoothing of $P(x;k_y)$ in the phase direction, for generating $E1(x;k_y)$. Then the k-space is only modulated where modulation allows a signal increase:

$$P_{def}(x;k_y) = P(x;k_y) \cdot \min(1; E2(x;k_y)),$$

with $$E2(x; k_y) = \frac{E1(x; -k_y)}{E1(x; k_y)}.$$

Thus, the modules of the two halves of the k-space are forced to be the same, regardless of the segmentation of the k-space.

In a third exemplary embodiment, flow artifacts may be suppressed by a heuristic search for a correction matrix $\Delta$ which is defined in a manner that corresponds to the entity and location of these artifacts in images.

In a fourth exemplary embodiment, one or more multichannel receive coils are used and receive coils sensitivity maps are used as an input, and for each image the computed sensitivity map is used in the fusion task, in which sensitivity values not matching the input sensitivity maps are corrected.

The correction matrix $\Delta$ is used for correcting image artifacts that do not respect said receive coil sensitivity maps, i.e. that were recognized because the signal ratio received by the receiving coils does not match the sensitivity map thereof.

This is because artifacts caused by motion, flow and other external interferences generally produce ghosting in images, that does not match the sensitivity of the receiving coils.

This additional information may assist in defining the variability range of $\Delta$.

In one embodiment, the following cost function $$\sum_{v=1}^{N_{Voxel}} \sigma_{Coils}^2 \left( \frac{m_{c(v)}}{e_{c(v)}} \right)$$

wherein $e_{c(v)}$ is the efficiency of the coil c in the voxel v. The value $$M = \frac{m_{c(v)}}{e_{c(v)}}$$

is proportional to the actual signal intensity. The dispersion of M is a measure of ghosting artifacts.

In a further exemplary embodiment, the fidelity term is modified such to carry out a Hermitian symmetrization of acquired k-space data sets, and the iterative reconstruction is endowed with an additional phase constrained term, by means of a POCS, or other Hermitian symmetrization techniques, integrated in said iterative algorithm.

In a further exemplary embodiment, the correction matrix $\Delta$ is used to change the fidelity term in order to carry out a Hermitian symmetrization of k-space data sets.

Hermitian symmetry of k-space is an intrinsic feature in MRI of real object, thus it can potentially be applied to all the acquired k-space, provided that dephasing effects, like those due to chemical shift and/or field inhomogeneity are negligible.

Thus the fidelity term is changed to fulfill a Hermitian symmetry condition such as $$\|Fm_i - (Fm_i)^\dagger\|_2$$

where the $\dagger$ symbol designates the Hermitian conjugate operation.

A new y' may be used in the fidelity term $$y' = \frac{y + y^\dagger}{2}$$

It should be noted that y must be cleared of both constant and space-dependent errors, the latter being caused, for instance, by reading or phase-encoding offsets or by the receiving coil itself.

The constraints that impose the Hermitian symmetry should account for the deviations caused by T2 decay and motion artifacts.

In a further exemplary embodiment, Hermitian symmetrization of k-spaces is performed using a phase constraint.

In yet another exemplary embodiment, reconstruction is carried out by a POCS technique integrated in said iterative algorithm.

Thus, a further fidelity term is added to the function to be minimized, related to the k-space lines that have not been acquired, reference for such lines being their phase constraint reconstruction, which is obtained by a POCS technique.

The latter is calculated at each iteration according to the current estimate of the k-space, and is associated with a configurable weight, in the function.

The iterative algorithm may be implemented in various manners.

In a first variant embodiment, the iterative reconstruction algorithm involves minimization of said optimization function by means of periodic changes of the correction matrix $\Delta$.

The iterative algorithm does not minimize all the terms in each step. One step is the standard compressed sensing one. The successive adjusts the correction matrix $\Delta$ to minimize artifacts.

The presence of multiple constraints at each iteration may be theoretically advantageous, but may not be easily implemented, especially in the Conjugate Gradient technique, and may involve slow convergence.

In a second variant embodiment, the following steps are provided:

d) separately processing the sets of image data, particularly the k-spaces, for each iteration, to obtain two separate images, using a standard CS technique;

e) combining the images so obtained by an image fusion technique, thereby improving the SNR and suppressing artifacts;

f) using the difference between the image obtained by image fusion and the original image to identify the required corrections based on the expected artifacts; for this purpose the difference $\|m_i-m\|_2$, or a more efficient distance, is used;

g) incorporating the identified corrections into the correction matrix $\Delta$ to be used in the next iteration.

Finally, the best correction matrix may be assessed, such that $TV(m)+\|\Psi m\|_1$ is minimized, where m derives from the previous iteration.

Concerning the image fusion technique, image similarity may be investigated at global or local level.

Global techniques provide a single similarity value that describes the overall similarity of two images, whereas local techniques provide a similarity image or map that describes the local similarity of the two images. This classification shall not be intended as absolute, as in many cases a global similarity measure can be converted into a local similarity measure and vice versa.

In the method of the present disclosure, the similarity estimate may be used both in the equation (4), instead of the $L_2$ norm of image difference, and in the equation (5) to combine images for maximizing the information content.

Various global similarity indices may be used to evaluate the performances of image fusion algorithms.

In the equation (5), the image average may be replaced by methods that better increase similarity and image correlations:

pixel-to-pixel image product;
coherent complex sum only on widely correlated areas;
weighted image fusion with Principal Component Analysis (PCA);
image fusion with Wavelet transform.

Thus, the following image fusion techniques may be used:
Averaging
Product
PCA fusion
PCA fusion with edge information
Fusion on similarity map
   Correlation map
   Bhat-Nayar distance
   Universal Quality Index
   Deviation from the fitting line
   Mean-square error
   Mean absolute error The above features for MRI applications may be also used in ultrasound imaging, with appropriate changes known to the skilled person.

In this variant embodiment, the sets of image data are generated by ultrasound acquisitions.

In one improvement, the sets of image data are multiple composite B-mode reconstructions of the same image for speckle noise reduction.

For reducing the artifacts caused by motion, flow and other external interferences that generally produce ghosting in images, we can fuse the images of different channels based on their sensitivity map. The measured sensitivity map is compared with an a-priori sensitivity map and the most different sensitivity values (corresponding to image region with signal higher or lower than expected) will be replaced by using interpolated values. The new corrected map will be used for the fusion task. In particular, pixels of the image channel with a low sensitivity value are likely to be penalized in the fusion because there is the highest probability to find an artifact giving an overestimated sensitivity value.

What was described above concerning k-spaces in MRI may be used in US imaging, with two-dimensional Fourier transforms of the image or with the acquired image data itself.

The determination of the best undersampling scheme may lead to considerable hardware simplification in the ultrasonic probe, particularly to a lower complexity of the switch hardware required for management of the array of electroacoustic transducers.

A further advantage is a reduction of the transfer-rate from the acquisition terminal to the processing terminal, as well as a reduction of the data to be saved.

Undersampling during acquisition may assist in improving diagnostics in highly dynamic clinical applications, such as vascular and cardiac imaging, may improve the frame rate and hence real-time reconstruction in composite, i.e. duplex and triplex modes.

Finally, due to the higher acquisition speed it affords, undersampling may allow multi-angle views, without adversely and apparently affecting the frame-rate.

This may in turn impart a greater robustness to real-time vector field estimation, such as in the case of directional Doppler.

A particularly advantageous embodiment is that of ultrasound tomography devices, such as those disclosed in U.S. Pat. No. 7,699,783, U.S. Pat. No. 7,684,846 and U.S. Pat. No. 7,771,360, which are hereby incorporated by reference and shall be deemed to be part of the present application.

A schematic representation of such an ultrasound tomography device 13 is illustrated in FIG. 9. Such ultrasound devices 13 include an ultrasound transmitter 14, an ultrasound receiver 15, and a processor 11 configured to enable the ultrasound processing. Since ultrasound tomography devices are disclosed in the above cited U.S. patents, their detailed illustration herein is not essential for a proper understanding of the invention. Accordingly, the ultrasound device, and some of its components, are illustrated in the drawing in the form of graphical drawing symbols or labeled, e.g., labeled rectangular boxes.

In this technical field, sets of signals are acquired along planes acquired at different angles, the reflection information and the transmission information being used for image reconstruction.

The CS technique may be applied in standard fashion, by undersampling acquisitions at different angles.

The CS technique that was applied to multiple k-spaces as described above, may applied to multiple sets of acquired signals.

In a preferred embodiment, the sets of signals for the transmission information and the reflection information respectively may be related to each other by the above described image fusion techniques, for the case of images with different contrasts.

Object of the present disclosure is also a method of reconstructing an MRI or ultrasound biomedical image, based on compressed sensing and comprising the steps of:

a) exciting a body under examination with radio-frequency (RF) or ultrasound (US) pulses for generating signals;

b) acquiring an image data set from said generated signals, wherein said signals are acquired by pseudo-random undersampling;

c) reconstructing said image using a nonlinear iterative algorithm for minimizing an optimization function containing a term for image data sparsity in a predetermined domain and a term for finite differences of the image, with a data fidelity constraint term ensuring fidelity to the acquired image data as in the following equation:

$$f=\|F_u m-y\|_2+\lambda_1\|\Psi m\|_1+\lambda_2 TV(m)$$

wherein the acquired image data set is multiplied by a correction matrix Δ, which is calculated from a mathematical model of expected artifacts according to prior knowledge of such artifacts, for adjusting said fidelity term in such a way that the fidelity term ensures fidelity of the reconstructed image to the corrected acquired image data.

Object of the present disclosure is also a method of reconstructing one or more MRI or ultrasound biomedical images, based on compressed sensing and comprising the steps of:

a) exciting a body under examination with radio-frequency (RF) or ultrasound (US) pulses for generating signals;

b) acquiring image data from said generated signals, wherein said signals are acquired by pseudo-random undersampling;

c) reconstructing said one or more images using a nonlinear iterative algorithm for minimizing an optimization function containing a term for image data sparsity in a predetermined domain and a term for finite differences of the image, with a data fidelity constraint term ensuring fidelity to the acquired image data as in the following equation:

$$f=\|F_u m-y\|_2+\lambda_1\|\Psi m\|_1+\lambda_2 TV(m)$$

wherein two or more sets of image data are acquired from said generated signals, each data set being acquired in a different undersampling scheme and/or a different acquisition mode such as to make the expected and unavoidable artifacts incoherent;

for each iteration of said nonlinear iterative algorithm the data sets are separately processed and separate images from the data sets are reconstructed;

the final reconstructed images are combined to form a single image suppressing incoherent artifacts;

wherein for each step of the nonlinear iterative algorithm the following steps are carried out:

d) combining the obtained images by an image fusion technique;

e) using the differences between the image obtained by image fusion and the original images to identify the required corrections based on the expected artifacts;

f) incorporating the identified corrections into the correction matrix Δ to be used in the next iteration.

BRIEF DESCRIPTION OF THE DRAWINGS

These and other features and advantages of the present disclosure will appear more clearly from the following description of a few embodiments, illustrated in the annexed drawings, in which.

DETAILED DESCRIPTION OF THE PREFERRED EMBODIMENTS

Figure 1:
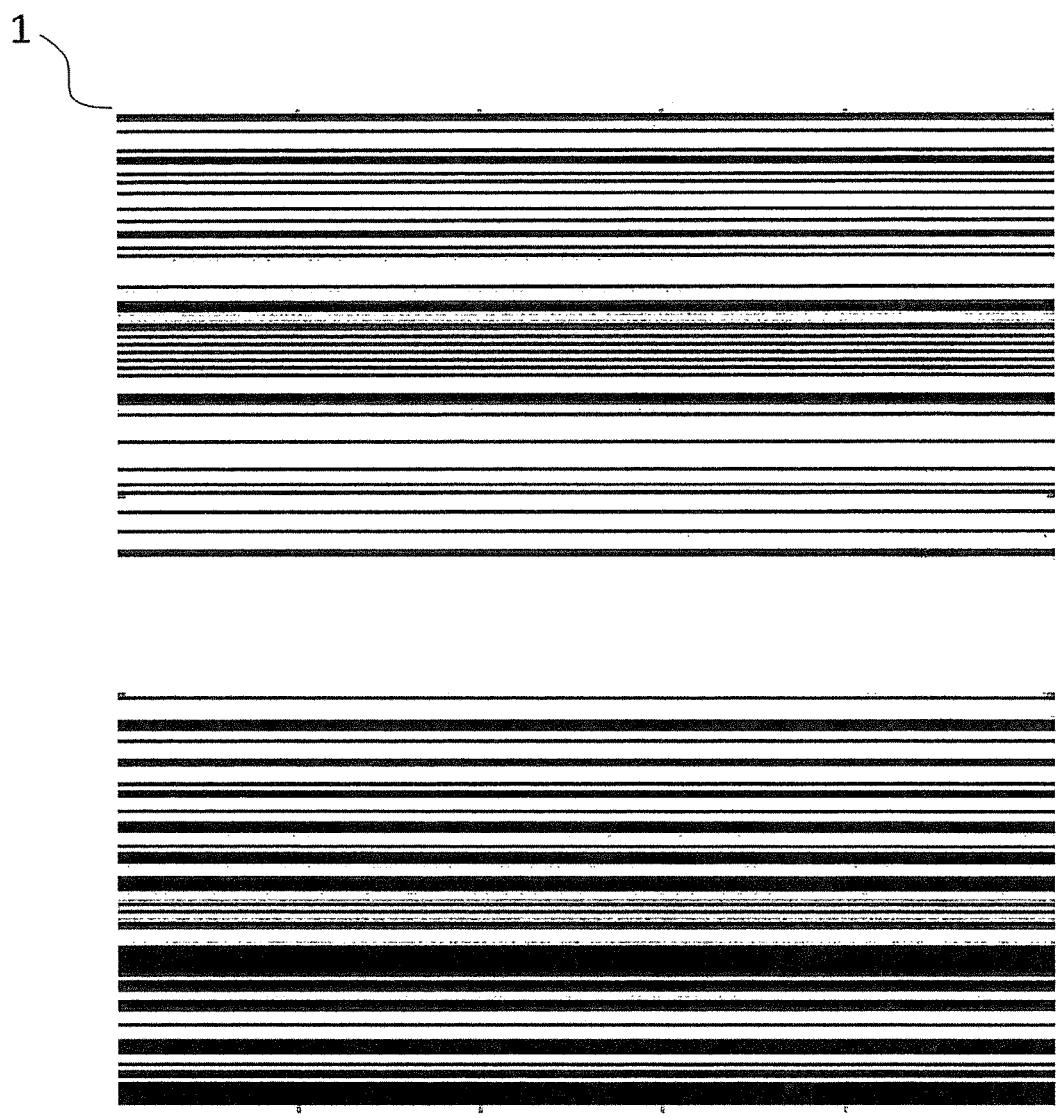
FIG. 1 shows an undersampling mask, as used in the CS technique.

FIG. 1 schematically shows an undersampling mask which is obtained in a pseudo-random manner, in which the missing samples are visible as black lines. Therefore, the k-space is not filled in continuous fashion, but is random at the edges, i.e. at high frequencies. K-space undersampling is controlled by a probability density function, which tends to assume lower values as it moves away from the center of the k-space.

In the case of FSE with series, the presence of acquisitions of multiple k-spaces of the same slice with symmetrized k-space segmentation, has an additional degree of freedom for undersampling optimization.

Figure 2A:
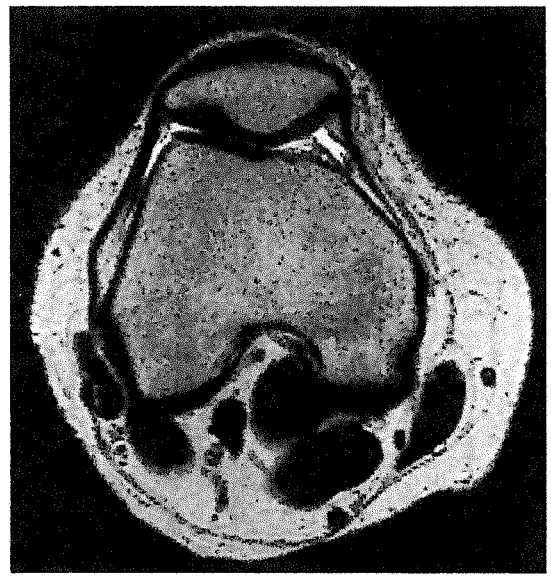
FIGS. 2a and 2b show a possible optimization of the undersampling technique that uses FSE sequences with multiple series (with an undersampling factor of 2.8)

FIG. 2a shows an example of complete reconstruction.

Figure 2B:
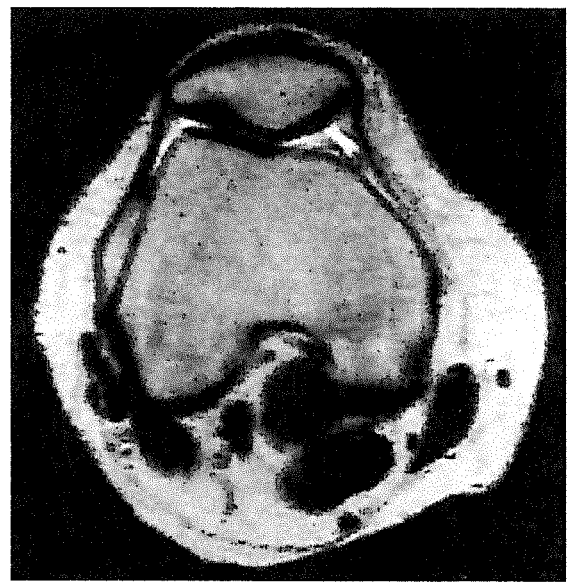

FIG. 2b shows the square root of the product of the CS reconstruction moduli of the two k-spaces with different masks.

In this case, the undersampling factor is 2.8, and particularly 80 acquisitions of a total of 224 were performed.

Figure 3A:
FIGS. 3a, 3b and 3c show an image obtained by Zero Filling (ZF), by CS without normalization and by CS with normalization.
Figure 3B:
Figure 3C:

FIGS. 3a, 3b and 3c show three reconstructions of the same images in different modes, with hyperintensities 2 being found.

FIG. 3a shows a ZF-reconstructed image, whereas FIG. 3b shows a non-normalized CS-reconstructed image. The image of FIG. 3c was reconstructed with normalization.

In this case, the undersampling factor is 1.23, and particularly 260 acquisitions of a total of 320 were performed.

As is clearly shown in FIG. 2a, a single hyperintensity 2 apparently causes undesired image flattening.

Hyperintensities may occur, for instance, in SE sequences, in the presence of magnetic field inhomogeneities or metal objects in the FOV.

In order to remove hyperintensities, noise is first suppressed, to obtain actual signal statistics, and then values exceeding predetermined threshold are excluded or smoothed.

Figure 4A:
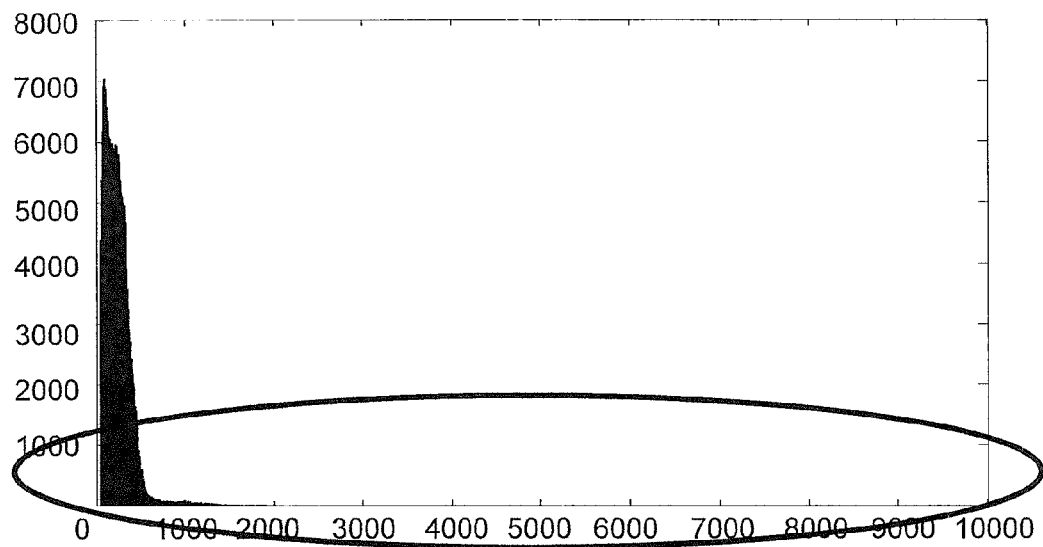
FIGS. 4a and 4b show normalization with removal of hyperintensities.
Figure 4B:
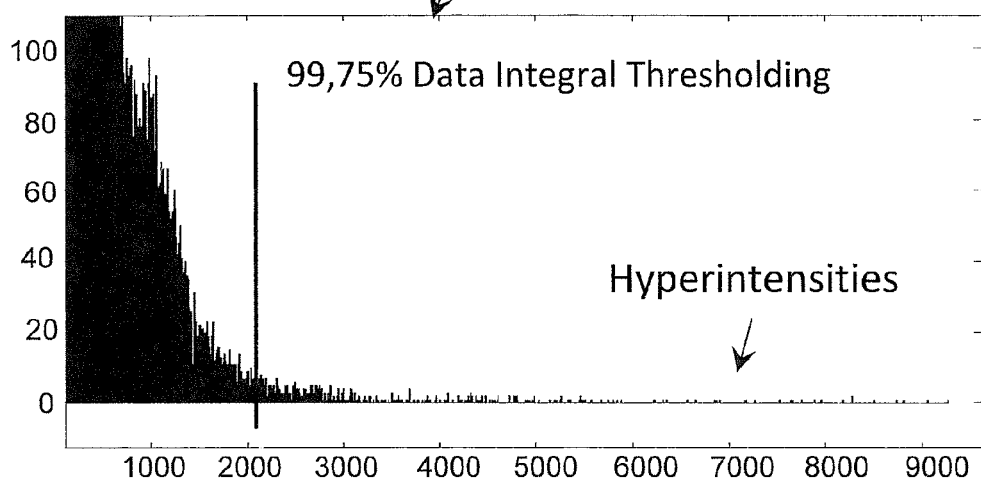

FIG. 4a shows the signal distribution after noise suppression, whereas FIG. 4b shows how hyperintensities are discarded by removing values exceeding a predetermined threshold.

As shown in FIGS. 5a to 5d, a combination of POCS and CS may improve image quality in SE sequences with undersampling, irrespective of Half Fourier acquisition.

Figure 5A:
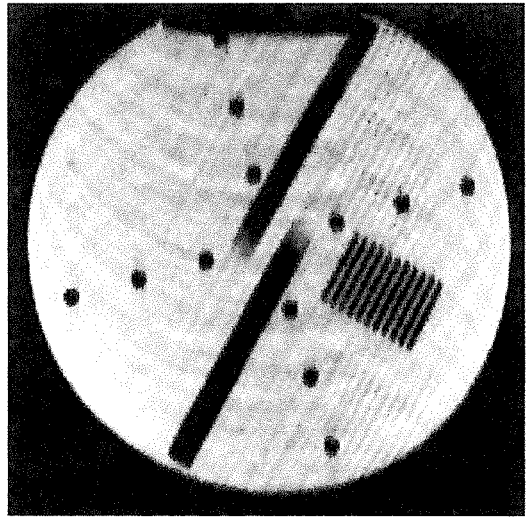
FIGS. 5a, 5b, 5c and 5d show an image reconstructed by ZF, by CS only, by POCS only, by POCS and CS.
Figure 5B:
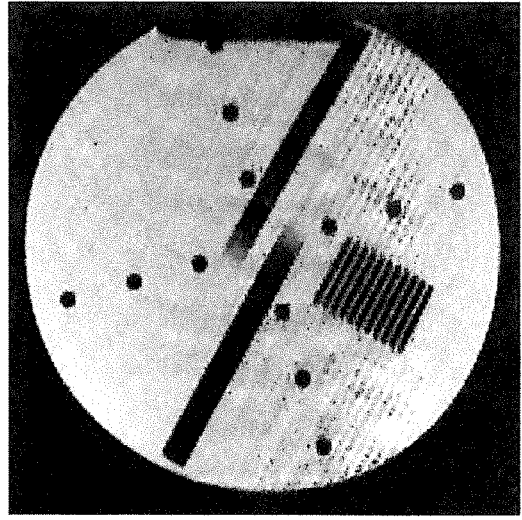
Figure 5C:
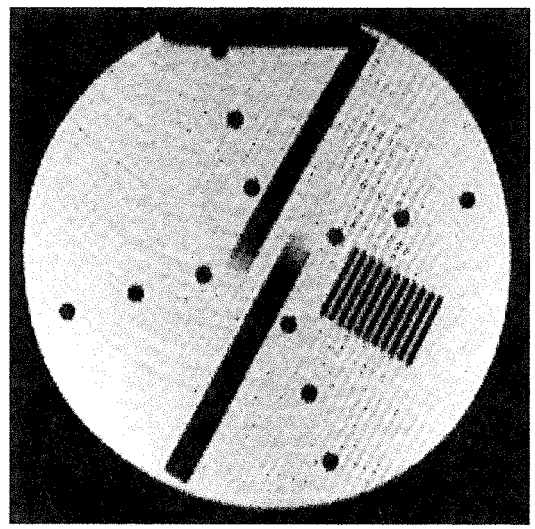
Figure 5D:
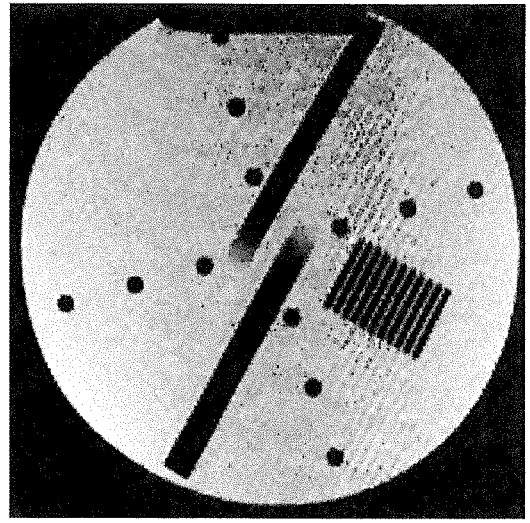
Figure 6:
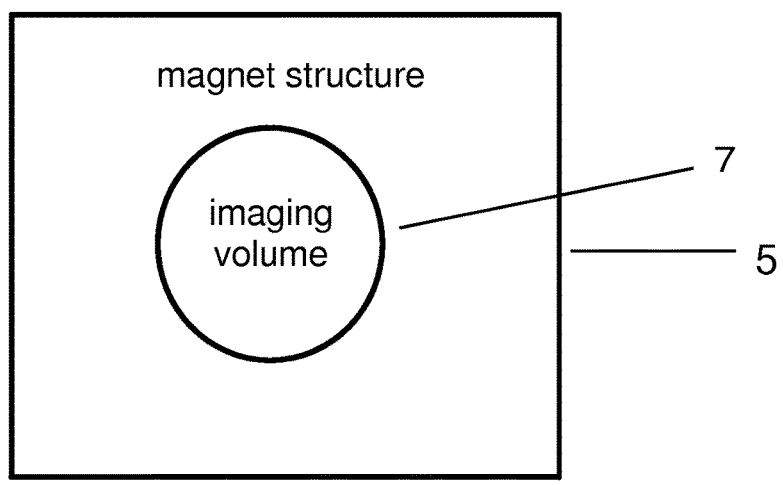
FIG. 6 shows a schematic representation of a magnet structure with an imaging volume therein.
Figure 7:
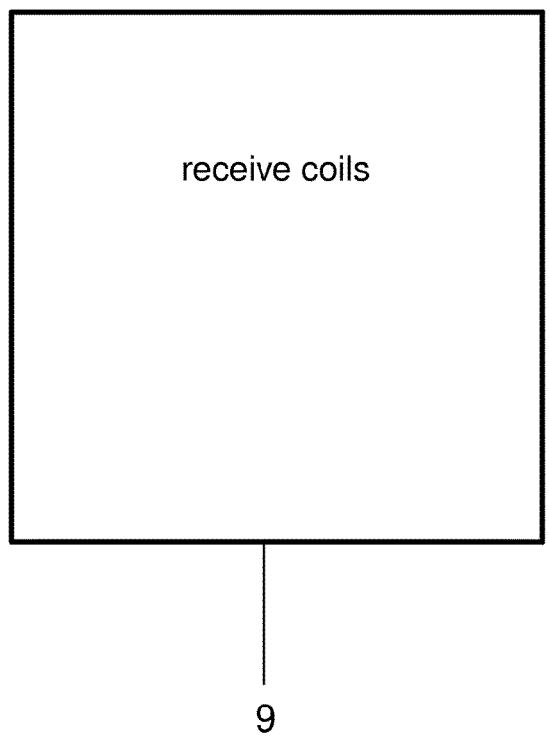
FIG. 7 is a schematic representation of multichannel receive coils.

The image of FIG. 5d, in which POCS and CS are combined, has a better quality than the ZF reconstruction of FIG. 5a, the CS reconstruction of FIG. 5b and the POCS reconstruction of FIG. 5c.

For these figures, an undersampling factor of 3 was used, and particularly 86 acquisitions of a total of 256 were performed. This is reflected by a reduction of the scan time to ⅓.

The iterative POCS process may be repeated at each CS iteration and generates a complete k-space: a further L2-norm fidelity term on POCS-generated data to fill the missing data, may be associated, by an appropriate coefficient $\lambda_{POCS}$ to the CS function to be minimized.

With the POCS constrains, the problem of global minimization may have a faster convergence.

Figure 8:
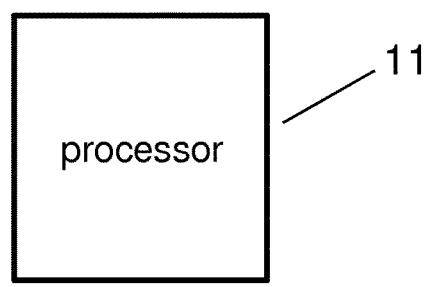
FIG. 8 shows a schematic representation of a processor.
Figure 9:
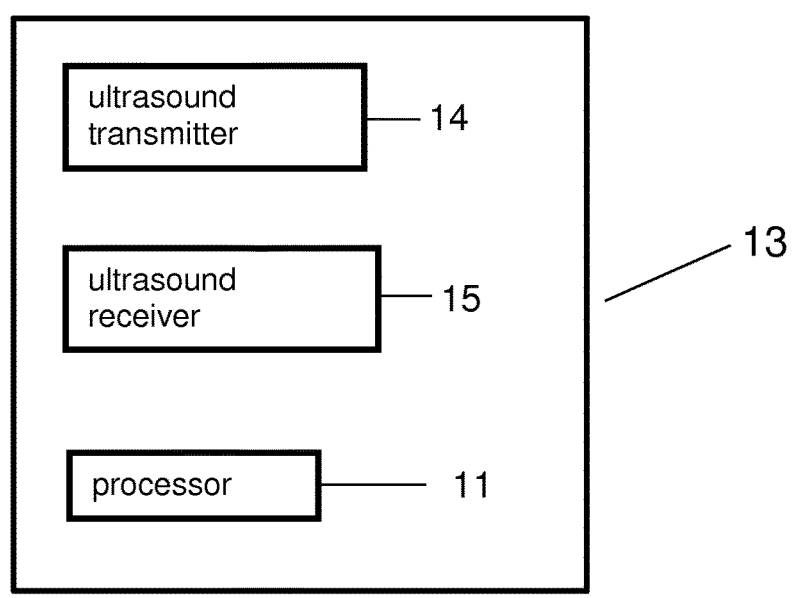
FIG. 9 is a schematic representation of an ultrasound tomography device.

In order to perform the methods disclosed herein, an MRI or ultrasound device includes a processor 11, which is schematically illustrated in FIG. 8. The processor 11 is configured to perform the claimed methods. Since a processor is a conventional feature, and its detailed illustration is not essential for a proper understanding of the invention, it is illustrated in the drawing in the form of a graphical drawing symbol or a labeled representation, e.g., a labeled rectangular box.

The present disclosure may be embodied in many different forms. While illustrative embodiments of the invention have been described herein, the present invention is not limited to the various preferred embodiments described herein, but includes any and all embodiments having equivalent elements, modifications, omissions, combinations (e.g. of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to". The language "present invention" or "invention" should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features.

A magnet structure 5 with an imaging volume 7 is provided, the magnet structure 5 having one or more apertures for access to said imaging volume, a center 7 of the magnet structure 5 being identified as a central position of the imaging volume 7 among these apertures, data normalization being performed by weighting the image with an attenuation factor that increases with the distance from the center of the magnet structure. Since the magnet structure is a conventional feature, and its detailed illustration is not essential for a proper understanding of the invention, it is illustrated in the drawing in the form of a graphical drawing symbol or a labeled representation, e.g., a labeled rectangular box.

One or more multichannel receive coils 9 are used and receive coils sensitivity maps are used as an input, and for each image a computed sensitivity map is used in a fusion task, in which sensitivity values not matching the sensitivity maps are corrected. Since the multichannel receive coils are conventional features, and their detailed illustration is not essential for a proper understanding of the invention, they are illustrated in the drawing in the form of a graphical drawing symbol or a labeled representation, e.g., a labeled rectangular box.

In this disclosure and during the prosecution of this case, the following abbreviated terminology may be employed: "e.g." which means "for example", and "NB" which means "note well".

The invention claimed is:

1. A method of reconstructing an MRI or ultrasound biomedical image, based on compressed sensing, the method comprising:
   a) generating signals by exciting a body under examination with radiofrequency (RF) or ultrasound (US) pulses;
   b) acquiring image data from said generated signals, wherein said image data is acquired by pseudo-random undersampling;
   c) reconstructing said MRI or ultrasound biomedical image using a nonlinear iterative algorithm for minimizing an optimization function containing a term for image data sparsity in a predetermined domain and a term for finite differences of the image, with a data fidelity constraint term ensuring fidelity to the acquired image data;
   wherein
   two or more sets of image data are acquired from said generated signals, each image data set being acquired in a different undersampling scheme, or a different acquisition mode such as to make expected and unavoidable artifacts incoherent;
   each of the acquired image data sets is multiplied by a correction matrix, which is calculated from a mathematical model of expected artifacts according to prior knowledge of such artifacts, for adjusting said data fidelity constraint term in such a way that the data fidelity constraint term ensures fidelity of the reconstructed MRI or ultrasound biomedical image to the acquired image data sets;
   for each iteration of said nonlinear iterative algorithm the data sets are processed to generate a combination image which is faithful to the acquired data but not to the incoherent artifacts, thereby leading to suppression of said artifacts;
   wherein:
   the data fidelity constraint term is adjusted in such a way that the data fidelity constraint term ensures fidelity of the reconstructed MRI or ultrasound biomedical image to the corrected acquired image data as in the following equation:

$$f = \sum_i \|F_{u_i} m - \Delta_i y_i\|_2 + \lambda_1 \|\Psi m\|_1 + \lambda_2 TV(m);$$

wherein:
   the index of each image data set is i,
   the different undersampling schemes are denoted by $u_i$,
   the correction matrix is denoted by $\Delta_i$,
   m is the combination image;
   $F_{u_i}$ is a Fourier transform;
   y is k-space;
   $\lambda_1$ and $\lambda_2$ are Projection Onto Convex Sets (POCS) coefficients;
   $\psi$ is a transform in a domain; and
   TV is Total Variation.

2. The method as claimed in claim 1, wherein each step of the nonlinear iterative algorithm further comprises:
   d) processing the two or more sets of image data independently with a Compressed Sensing iteration to obtain images from the acquired sets of image data;
   e) combining the obtained images by an image fusion technique;

f) using differences between the image obtained by image fusion and the original images to identify required corrections based on the expected artifacts; and g) incorporating the identified required corrections into the correction matrix to be used in a next iteration.

3. The method as claimed in claim 2, wherein data sets of images with different contrast information are acquired, and said image fusion technique comprises the use of a map of the physical quantity that drives the difference among the images, according to an acquisition sequence type, wherein the generated map is suitable for use as an output.

4. The method as claimed in claim 1, wherein said image datasets are k-space data sets generated by 2D or 3D MRI acquisitions.

5. The method as claimed in claim 1, further comprising data normalization performed by exclusion or smoothing of values exceeding a predetermined threshold.

6. The method as claimed in claim 1, wherein a magnet structure with an imaging volume is provided, the magnet structure having one or more apertures for access to said imaging volume, a center of the magnet structure being identified as a central position of the imaging volume among these apertures, data normalization being performed by weighting the image with an attenuation factor that increases with the distance from the center of the magnet structure.

7. The method as claimed in claim 1, wherein sequential averages are determined between the data sets.

8. The method as claimed in claim 1, wherein phase cycling is performed one or more times, for Balanced Steady-State Free Processing excitation sequences (bSSFP).

9. The method as claimed in claim 1, wherein a Fast Spin Echo excitation sequence is used and wherein the mapping of echoes of two or more k-space data sets are permuted to obtain different envelope profiles.

10. The method as claimed in claim 2, wherein data sets of images with different contrast information are acquired, and said image fusion technique comprises the use of a map of the physical quantity that drives the difference among the images, according to an acquisition sequence type.

11. The method as claimed in claim 10, wherein multi-echo spin-echo sequences are used, and the image fusion technique comprises T2 mapping by monoexponential best-fit of the signal for each pixel or voxel, corresponding T2 error mapping, the iterative reconstruction process including rank-2 minimization of the T2 error map.

12. The method as claimed in claim 10, wherein a Double Echo Steady State Gradient Echo sequence is used, and the image fusion technique comprises the calculation of a map of the logarithm of the ratio between the images.

13. The method as claimed in claim 1, wherein the correction matrix is used for correcting motion artifacts and is calculated by estimating a predetermined displacement value in read and phase directions in real world and incorporating it as a phase shift in k-space data sets at a predetermined acquisition time.

14. The method as claimed in claim 1, wherein the correction matrix is used for correcting k-space inconsistencies induced by echo position and phase errors in read and phase directions in a Fast Spin Echo (FSE) acquisition.

15. The method as claimed in claim 1, wherein the correction matrix is used for correcting T2 decay induced artifacts in Fast Spin Echo sequences.

16. The method as claimed in claim 1, wherein one or more multichannel receive coils and receive coil sensitivity maps are used, and for each image a computed sensitivity map is used in a fusion task, in which sensitivity values not matching the sensitivity maps are corrected.

17. The method as claimed in claim 1, wherein the data fidelity constraint term is modified such to carry out a Hermitian symmetrization of acquired k-space data sets, and the iterative reconstruction is endowed with an additional phase constrained term, by means of a Projection Onto Convex Sets (POCS), or other Hermitian symmetrization techniques, integrated in said iterative algorithm.

18. The method as claimed in claim 1, wherein said iterative reconstruction algorithm involves minimization of said optimization function by means of periodic changes of the correction matrix.

19. The method as claimed in claim 1, wherein the image data sets are generated by 2D or 3D ultrasound acquisitions.

20. The method as claimed in claim 19, wherein the image data sets are related to reflection information and transmission information respectively, said image being designed to be generated by an image fusion technique.

21. The method as claimed in claim 1, wherein the image data sets are multiple composite B-mode reconstructions of the same image for speckle noise reduction.

22. The method as claimed in claim 1, wherein the method is a method of reconstructing an MRI biomedical image.

23. The method as claimed in claim 1, wherein the method is a method of reconstructing an ultrasound biomedical image.

24. A magnetic resonance imaging (MRI) apparatus, comprising MRI hardware including a magnet structure and multi-channel receive coils and a processor configured to enable the MRI hardware to perform the method of claim 1.

25. An ultrasound imaging device comprising an ultrasound transmitter, an ultrasound receiver, and a processor configured to perform the method of claim 1.

26. A method of reconstructing an MRI or ultrasound biomedical image, based on compressed sensing, the method comprising:

a) generating signals by exciting a body under examination with radio-frequency (RF) or ultrasound (US) pulses;

b) acquiring an image data set from said generated signals, wherein said generated signals are acquired by pseudo-random undersampling;

c) reconstructing said MRI or ultrasound biomedical image using a nonlinear iterative algorithm for minimizing an optimization function containing a term for image data sparsity in a predetermined domain and a term for finite differences of the image, with a data fidelity constraint term ensuring fidelity to the acquired image data wherein the acquired image data set is multiplied by a correction matrix, which is calculated from a mathematical model of expected artifacts according to prior knowledge of such artifacts, for adjusting said fidelity term in such a way that the fidelity term ensures fidelity of the reconstructed image to the acquired image data set;

wherein:

the data fidelity constraint term is adjusted in such a way that the data fidelity constraint term ensures fidelity of the reconstructed MRI or ultrasound biomedical image to the corrected acquired image data as in the following equation:

$$f = \|F_u m - y\|_2 + \lambda_1 \|\Psi m\|_1 + \lambda_2 TV(m)$$

wherein:

m is the combination image;

$F_u$ is a Fourier transform;

y is k-space;

$\lambda_1$ and $\lambda_2$ are Projection Onto Convex Sets (POCS) coefficients;

ψ is a transform in a domain; and

TV is Total Variation.

27. The method as claimed in claim 26, wherein the method is a method of reconstructing an MRI biomedical image.

28. The method as claimed in claim 26, wherein the method is a method of reconstructing an ultrasound biomedical image.

29. A magnetic resonance imaging (MRI) apparatus, comprising MRI hardware including a magnet structure and multi-channel receive coils and a processor configured to enable the MRI hardware to perform the method of claim 26.

30. An ultrasound imaging device comprising an ultrasound transmitter, an ultrasound receiver, and a processor configured to perform the method of claim 26.

31. A method of reconstructing one or more MRI or ultrasound biomedical images, based on compressed sensing, the method comprising:

a) generating signals by exciting a body under examination with radio-frequency (RF) or ultrasound (US) pulses;

b) acquiring image data from said generated signals, wherein said generated signals are acquired by pseudo-random undersampling;

c) reconstructing said one or more MRI or ultrasound biomedical images using a nonlinear iterative algorithm for minimizing an optimization function containing a term for image data sparsity in a predetermined domain and a term for finite differences of the image, with a data fidelity constraint term ensuring fidelity to the acquired image data;

wherein two or more sets of image data are acquired from said generated signals, each data set being acquired in a different undersampling scheme or a different acquisition mode such as to make expected and unavoidable artifacts incoherent;

for each iteration of said nonlinear iterative algorithm the data sets are separately processed and separate images from the data sets are reconstructed;

the one or more reconstructed images are combined to form a single image suppressing incoherent artifacts;

wherein for each step of the nonlinear iterative algorithm the following steps are carried out:

d) combining the obtained images by an image fusion technique;

e) using the differences between the image obtained by image fusion and the reconstructed images to identify required corrections based on the expected artifacts;

f) incorporating the identified corrections into a correction matrix to be used in a next iteration, wherein:

the data fidelity constraint term is adjusted in such a way that the data fidelity constraint term ensures fidelity of the reconstructed MRI or ultrasound biomedical image to the corrected acquired image data as in the following equation:

$$f = \|F_u m - y\|_2 + \lambda_1 \|\Psi m\|_1 + \lambda_2 TV(m)$$

wherein:

m is the combination image;

$F_u$ is a Fourier transform;

y is k-space;

$\lambda_1$ and $\lambda_2$ are Projection Onto Convex Sets (POCS) coefficients;

ψ is a transform in a domain; and

TV is Total Variation.

32. The method as claimed in claim 31, wherein the method is a method of reconstructing an MRI biomedical image.

33. The method as claimed in claim 31, wherein the method is a method of reconstructing an ultrasound biomedical image.

34. A magnetic resonance imaging (MRI) apparatus, comprising MRI hardware including a magnet structure and multi-channel receive coils and a processor configured to enable the MRI hardware to perform the method of claim 31.

35. An ultrasound imaging device comprising an ultrasound transmitter, an ultrasound receiver, and a processor configured to perform the method of claim 31.

* * * * *